United States Patent
Kuczynski et al.

(10) Patent No.: US 7,578,850 B2
(45) Date of Patent: Aug. 25, 2009

(54) UNICONDYLAR KNEE IMPLANT

(75) Inventors: John D. Kuczynski, Pequannock, NJ (US); Mikhail Kvitnitsky, Clifton, NJ (US)

(73) Assignee: Uni-Knee, LLC, Clifton, NJ (US)

( * ) Notice: Subject to any disclaimer, the term of this patent is extended or adjusted under 35 U.S.C. 154(b) by 0 days.

(21) Appl. No.: 11/304,958

(22) Filed: Dec. 14, 2005

(65) Prior Publication Data

US 2006/0235537 A1    Oct. 19, 2006

Related U.S. Application Data

(60) Provisional application No. 60/672,211, filed on Apr. 18, 2005.

(51) Int. Cl.
*A61F 2/38*    (2006.01)
(52) U.S. Cl. .................. 623/20.34; 623/20.21; 623/20.3
(58) Field of Classification Search ................ 623/20.3, 623/20.18, 20.15, 20.21, 20.35, 20.31, 20.32, 623/20.34; 606/88
See application file for complete search history.

(56) References Cited

U.S. PATENT DOCUMENTS

| | | | |
|---|---|---|---|
| 4,714,474 A | 12/1987 | Brooks, Jr. et al. | |
| 4,719,908 A | 1/1988 | Averill et al. | |
| 4,795,468 A | 1/1989 | Hodorek et al. | |
| 4,938,769 A * | 7/1990 | Shaw .................. | 623/20.15 |
| 4,963,153 A * | 10/1990 | Noesberger et al. ...... | 623/20.32 |
| 5,037,439 A | 8/1991 | Albrektsson et al. | |
| 5,074,880 A | 12/1991 | Mansat | |
| 5,171,276 A | 12/1992 | Caspari et al. | |
| 5,201,768 A | 4/1993 | Caspari et al. | |
| 5,203,807 A | 4/1993 | Evans et al. | |
| 5,207,711 A | 5/1993 | Caspari et al. | |
| 5,312,411 A | 5/1994 | Steele et al. | |
| 5,314,482 A | 5/1994 | Goodfellow et al. | |
| 5,326,361 A | 7/1994 | Hollister | |
| 5,336,266 A | 8/1994 | Caspari et al. | |
| 5,609,643 A | 3/1997 | Colleran et al. | |
| 5,871,546 A | 2/1999 | Colleran et al. | |
| 6,059,831 A | 5/2000 | Braslow et al. | |
| 6,090,114 A * | 7/2000 | Matsuno et al. ................ | 606/88 |
| 6,165,222 A * | 12/2000 | Hoeppner et al. ......... | 623/20.15 |
| 6,296,646 B1 | 10/2001 | Williamson | |
| 6,478,799 B1 | 11/2002 | Williamson | |

(Continued)

OTHER PUBLICATIONS

Harrington, Ian J., Static and Dynamic Loading Patterns in Knee Joints with Deformities. *The Journal of Bone and Joint Surgery, Incorporated* vol. 65-A, No. 2, Feb. 1983, 247-259.

(Continued)

*Primary Examiner*—David Isabella
*Assistant Examiner*—Suba Ganesan
(74) *Attorney, Agent, or Firm*—Matthew B. Dernier, Esq.; Gibson & Dernier LLP (57) ABSTRACT

A unicondylar knee implant system according to one embodiment includes a unicondylar femoral knee component having a single sagittal radius, a tibial bearing component, and a tibial tray component having a self-locking keel. The unicondylar knee implant system also provides for a locking mechanism for securing the tibial bearing component onto the tibial tray component. The unicondylar knee system allows for a simplified surgical technique, complete interchangeability between sizes, and a more MIS compatible implant system.

46 Claims, 11 Drawing Sheets

U.S. PATENT DOCUMENTS

| | | | |
|---|---|---|---|
| 6,494,914 | B2 | 12/2002 | Brown et al. |
| 6,554,838 | B2 | 4/2003 | McGovern et al. |
| 6,569,202 | B2 | 5/2003 | Whiteside |
| 6,797,006 | B2 | 9/2004 | Hodorek |
| 6,869,448 | B2 | 3/2005 | Tuke et al. |
| 6,942,700 | B2 | 9/2005 | Williamson |
| 7,172,597 | B2 * | 2/2007 | Sanford ............... 606/88 |
| 2002/0068979 | A1 * | 6/2002 | Brown et al. ............ 623/20.3 |
| 2002/0183760 | A1 | 12/2002 | McGovern et al. |
| 2003/0014122 | A1 | 1/2003 | Whiteside |
| 2003/0100953 | A1 | 5/2003 | Rosa et al. |
| 2003/0130665 | A1 | 7/2003 | Pinczewski et al. |
| 2003/0139817 | A1 | 7/2003 | Tuke et al. |
| 2003/0153923 | A1 | 8/2003 | Pinczewski et al. |
| 2003/0233149 | A1 | 12/2003 | Hodorek |
| 2004/0006394 | A1 | 1/2004 | Lipman et al. |
| 2004/0102852 | A1 | 5/2004 | Johnson et al. |
| 2004/0153164 | A1 | 8/2004 | Sanford et al. |
| 2005/0085920 | A1 | 4/2005 | Williamson |
| 2005/0125068 | A1 | 6/2005 | Hozack et al. |
| 2005/0171604 | A1 | 8/2005 | Michalow |

OTHER PUBLICATIONS

International Search report and Written Opinion of PCT/US06/02907.

International Preliminary Report on Patentability and Written Opinion of PCT/US06/02907.

* cited by examiner

+θ  −θ
FLEXION  HYPEREXTENSION

UNICONDYLAR KNEE IMPLANT

CROSS REFERENCE TO RELATED APPLICATIONS

The present application claims priority to Provisional Application No. 60/672,211 filed Apr. 18, 2005, the disclosure of which is hereby incorporated by reference.

BACKGROUND OF THE INVENTION

1. Field of the Invention

The present invention is related to an orthopedic medical device. In particular, the present invention is related to a unicondylar knee implant system.

2. Description of the Related Art

Orthopedic knee implant systems have been used for many years to treat patients with knee joints that have been damaged by trauma or disease, such as osteoarthritis, rhumetoid arthritis, and avascular neurosis. A knee arthroplasty resects, cuts, or resurfaces the damaged sections of the knee and replaces them with an endoprosthetic or implant.

Most knee implant systems are tricompartmental implants and the surgical procedure used with tricompartmental implants is commonly known as total knee arthroplasty. These implants are known as tricompartmental implants because they are used when the femur is prepared to receive an implant by resurfacing or resecting the three compartments of the distal femur, i.e., the medial and lateral condyles and the trochlear groove. Regardless of the type of implant used, all arthroplasties require the bone to be specifically prepared to receive a corresponding implant by resecting, resurfacing, or deforming the bone to accept the implant.

Most knee implant systems are modular systems with multiple sizes and thicknesses and degrees of interchangeability between the sizes. For example, a typical total knee implant system may consist of 6 femoral implant sizes, 6 tibial tray implant sizes, and 6 tibial bearing implant sizes with each tibial bearing size having 7 different thicknesses. The various implant sizes are required to meet the various size bones of patients. Typical implant systems often allow interchangeability between sizes for example; a medium size femoral implant may be used with a single larger size tibial implant and tibial bearing implant to match the specific needs of a patient. However, most knee implant systems are limited with regards to the range of interchangeability between sizes; for example, the largest size femoral implant component typically cannot be used and is not compatible with the smallest size tibial tray and tibial bearing component. This is because such a high degree of mismatch between sizes often affects the range of constraint designed into the implants. Moreover, conventional implant systems require a prepared bone surface to be further resected or resurfaced whenever a different size implant is required, adding to the overall surgical time, complexity of the surgery, and bone loss.

Tibial tray implants typically have some sort of keel associated with the tibial tray to provide a level of initial fixation. Other methods if initial fixation have also been used with tibial trays, such as spikes protruding from the bone engaging surface of the implant or screws inserted through the tibial tray into the bone. However, the use of screws has been associated with osteolysis and provides a pathway for debris to enter the tibial bearing tibial tray interface. Typical keel designs have simply been of a straight cylindrical or vertical plane geometry extending from the bone engaging surface of the tibial tray implant. Accordingly, these tibial tray keel designs provide minimal initial fixation and require a significant amount of exposure of the knee joint to implant as these designs are implanted with a top down approach. A top down approach is defined for example, as implanting the tibial tray into a prepared horizontal tibial surface when the tibia is set in a vertical orientation.

Minimally invasive surgery ("MIS") has become of great interest within the field of orthopedics. Thus, unicondylar or unicompartmental knee implants have become of great interest in the orthopedic industry due to their small size and applicability to MIS surgical approaches. Unicondylar knee implants are designed to replace only a single condyle (e.g., the medial or lateral condyle) of the distal femur.

Minimally invasive knee surgery has not yet been fully defined. However, minimally invasive knee surgery has generally been considered to include a smaller incision. A typical incision length for a total knee replacement can be up to 10 to 12 inches long. The general theory behind MIS is that with a smaller incision length, the patient will be able to recover from surgery faster.

Generally, the clinical outcomes for unicondylar knee implants have varied. Studies have reported long term survival rates for unicondylar implants to be less than that of comparable total knee implants. One particular cause for such discrepancies is due to technique associated with the implant.

The unicompartmental implant most studied is the Oxford implant. The Oxford implant is a mobile bearing unicompartmental implant. Moreover, the Oxford implant is implanted with a free-hand technique, i.e., where the bone resections are not guided by instrumentation. Thus, the clinical outcomes for these implants have varied depending upon the particular surgeon implanting the device. Accordingly, a surgeon proficient in this technique is more likely to have a good outcome whereas a less experienced surgeon is more likely not to have as good an outcome with this implant.

Recent advancements in unicondylar knee implants have resulted in techniques that employ instrumented techniques for implantation. U.S. Pat. No. 6,554,838 to McGovern et al. discloses a unicondylar knee implant that uses a guided burring technique to implant the femoral component. However, instrumentation for such implant designs are bulky and required to be operated from various angles as opposed to a predominantly anterior orientation. Accordingly, such instrument designs are not completely conducive to minimally invasive surgical approaches or a reproducible surgical result.

U.S. Pat. No. 5,326,361 to Hollister discusses an alternative approach to knee biomechanics that views the knee to move through a range of motion from flexion to extension about a single axis of rotation. This view is a departure from the traditional view that the knee profile is defined by multiple centers of curvature and thus multiple axis of rotation. In particular U.S. Pat. No. 5,326,361 discloses a total knee implant system having a single cross-sectional sweep from zero to over 120 degrees.

The development of orthopedic implant designs has been moving towards meeting the requirements of high demand patients. Patients nowadays are requiring more from their implants and since patients are living longer these days, are requiring implants to last longer. Accordingly, developments have been made in materials used to make orthopedic implants to improve implant survival rates, such as the use of cobalt chromium alloys, titanium alloys, diamond-like coatings, ceramics, hydroxyapatite coatings, and ultra-high molecular weight polyethylene materials. Moreover, implant designs have changed to meet the ever increasing demands of patients, for example the general population of Asian countries prefers implants that allow for a higher degree of flexion than traditional implants.

The relationship between flexion angle and femoral-tibial conformity is determined by gait analysis studies. For example, gait data for Caucasian population is presented in Harrington I. J., et al. "Static and Dynamic Loading Patterns in Knee Joints with Deformities", J.B.J.S., Vol. 65-A, No. 2, February 1983, pp. 247-259. Based upon such studies the relationship between flexion angle and femoral-tibial conformity varies for different genders and races.

Thus, there is a need for a unicompartmental knee implant system that addresses the above mentioned deficiencies in current implant designs while simultaneously being suitable for minimally invasive surgical techniques.

BRIEF SUMMARY OF THE INVENTION

The present invention provides for a unicondylar knee prosthesis having a tibial bearing component, a tibial tray component, and a femoral knee component. The present invention also provides for a locking mechanism for locking the tibial bearing component onto the tibial tray component.

The tibial bearing component includes a top portion having an articulating surface and a bottom portion. The bottom portion further includes at least one flexible catch for engaging a corresponding latch on the tibial tray component. The tibial bearing component's flexible catch and the tibial tray component's latch form part of the locking mechanism for securing the tibial tray bearing component onto the tibial tray component. Preferably, the locking mechanism has at least four flexible catches while the tibial tray component has two latches. The flexible catches are configured to have an opening on the bottom portion of the bearing component facing the peripheral vertical rim of the tibial tray component when attached. The opening is further configured to be in fluid communication with a second opening on the distal surface of the bottom portion of the tibial bearing component. The locking mechanism also includes a peripheral vertical rim on the tibial tray component and at least one latch or lip extending from the peripheral vertical rim.

The tibial tray component includes a tray member and a keel connected to a distal surface of the tray member. The keel further includes a vertical keel section extending from the distal surface of the tray member and a keel foot having a posterior slope and a posterior taper. The keel is a self-locking keel that generates a securing force to secure the tibial tray onto a prepared tibia.

The femoral knee component of the unicondylar knee prosthesis includes a bone engaging surface and an articulating surface having a single sagittal radius of curvature from about 10 degrees of hyperextension to about 140 degrees of flexion. The femoral knee component can further include a posterior flange and at least one peg, angled relative to the posterior flange, for engaging a distal femur. Preferably the peg is angled at about 25 degrees relative to the posterior flange. More preferably, the femoral knee component has two substantially parallel pegs angled about 25 degrees from the posterior flange. The femoral knee component can also be configured to have a single medial-lateral radius of curvature. The single medial-lateral radius of curvature can be at about 38 mm.

The present invention also provides for a keel for a device. The keel includes a vertical keel section for extension from a surface of the device. The keel foot is connected to the end of the vertical keel section and has a sloped and tapered configuration. This keel can be used for devices such as an orthopedic tibial prosthesis of a unicondylar or total knee implant.

Another aspect of the present invention provides for a unicondylar femoral knee implant system having at least two unicondylar femoral knee implants. The unicondylar femoral knee implant system has a distal bone engaging surface having an anterior end, a distal-to-posterior chamfer bone engaging surface disposed between the distal and the posterior bone engaging surface. The unicondylar femoral knee implant system also has at least one peg extending from the distal bone engaging surface at a constant distance from the anterior end for the at least two unicondylar femoral knee implants.

The present invention also provides for the aforementioned prosthesis and devices to further include biological coatings. Such coatings may include hydroxyapatite and Osteogenic Protein-1 (OP1).

BRIEF DESCRIPTION OF THE DRAWINGS

Further aspects and advantages of the invention will become apparent from the following description and claims, and from the accompanying drawings, wherein:

FIG. 9b is a detailed perspective superior view of a latch protruding from a peripheral vertical rim of the tibial tray implant of FIG. 9a;

FIG. 10 is a perspective inferior view of the embodiment of the tibial tray implant of FIG. 9a.

DETAILED DESCRIPTION OF THE INVENTION

As used herein, the following definitional terms apply. The term "unicondylar" is synonymous with "unicompartmental." "Anterior" and "posterior" mean nearer to the front or the back of the body respectively. "Proximal" and "distal" mean nearer and farther from the center of the body respectively. "Medial" and "lateral" mean nearer or farther from the median plane respectively. The median plane is an imaginary, vertical plane that divides the body into a right and left half. The coronal plane is an imaginary, vertical plane that divides the body into a front half and a back half. "Superior" and "inferior" mean above or below respectively. For example, the distal femur has a medial and lateral condyle that are superior to the proximal tibia. "Sagittal" means a side profile.

The present invention allows for complete interchangeability between all sizes of the femoral and tibial components. In an embodiment, the unicondylar knee prosthesis is of a modular design with multiple sizes for its femoral, tibial tray, and tibial bearing components, along with multiple thicknesses for its tibial bearing components. The tibial tray components can have about 6 sizes growing in size in both the anterior/ posterior and medial/lateral directions. The tibial bearing components can have about 6 sizes growing in both the anterior/posterior and medial/lateral directions. The femoral components have a left and right component with each component having about 6 sizes growing in both the anterior/posterior and medial/lateral directions. Moreover, the smallest femoral component can be used with the largest tibial component and vice versa, thus allowing for unlimited interchangeability between sizes. As a result, the present inventive system can be used for any patient with extreme variations between tibial and femoral sizes.

Referring now to the drawings in detail wherein like numerals refer to like elements throughout the several views, FIGS. 1-11 represent embodiments of the present invention for a unicondylar knee implant.

Figure 1:
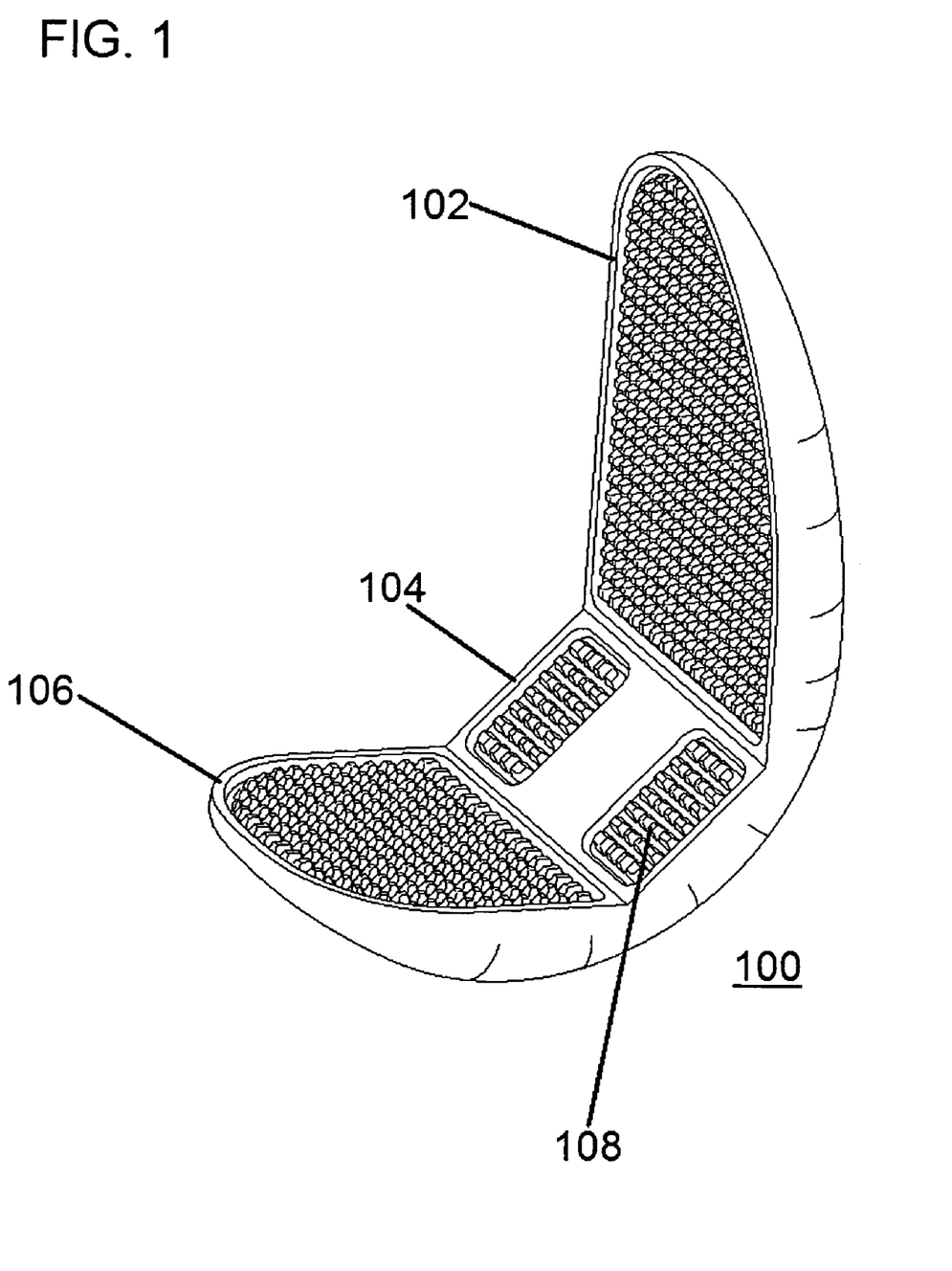
FIG. 1 is a perspective view of an embodiment of a unicondylar femoral knee implant of the present invention.

FIG. 1 is a perspective view of an embodiment of a unicondylar femoral knee component 100. Orientation references, such as medial or lateral, are given assuming the femoral component is implanted in the medial compartment of a patient's left knee. However, it will be understood that the same femoral component can be implanted into the lateral compartment of the opposite knee.

Figure 2A:
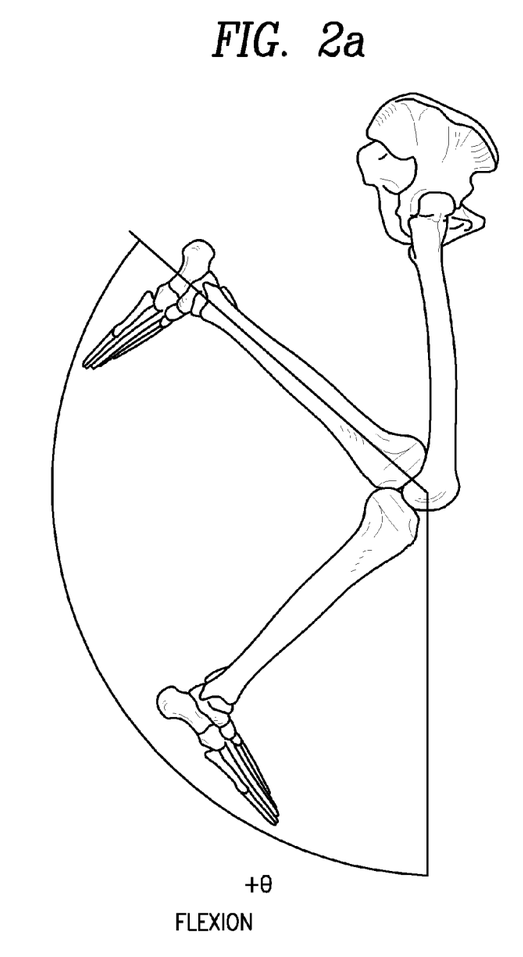
FIGS. 2a and 2b are illustrations of the knee joint at flexion and hyperextension.
Figure 2B:
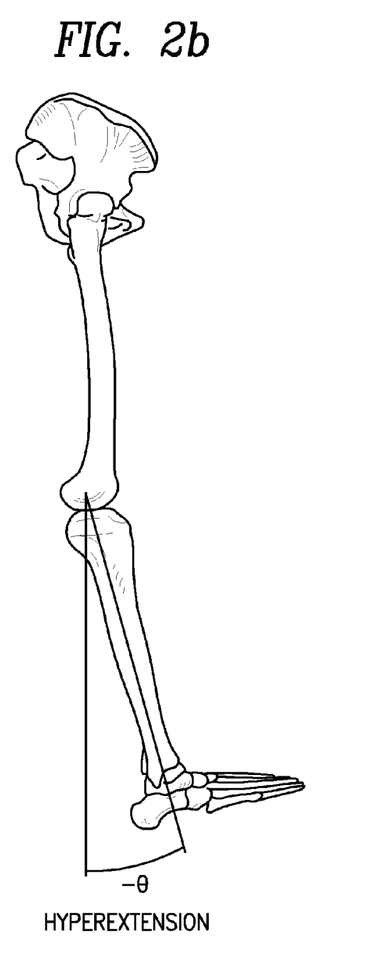

Surfaces 102, 104, and 106 of the present embodiment's femoral knee component define the bone engaging or interface surfaces. A bone engaging or interface surface as used herein is used to describe the non-articulating, attachment side of the implant. The bone engaging or interface surface does not necessarily need to contact the bone and may instead only come in contact with an adhesive such as bone cement. The bone interface surfaces consist of a distal surface 102, a posterior surface 106, and a distal-to-posterior chamfer surface 104 disposed between the distal surface 102 and the posterior surface 106. The posterior bone interface surface 106 is at an angle of about 83 degrees with respect to the distal bone interface surface 102. The distal-to-posterior chamfer surface 104 is equiangular from the distal bone interface surface 102 and the posterior bone interface surface 106. Equiangular is defined as being at the same angle. By defining a chamfer surface 104 equiangular to both the distal 102 and posterior 106 bone interfaces, the articulating surface of the femoral component is allowed to maintain a constant radius of curvature that extends from the distal portion of the femur through the distal-to-posterior chamfer and onto the posterior portion of the femoral knee component 100. The femoral knee component's constant radius of curvature when viewed from a sagittal profile can be defined by a single sagittal radius of curvature. The single sagittal radius of curvature starts at about 10 degrees of hyperextension, and preferably at about 1 degree of hyperextension, and extends to about 145 degrees of flexion. As shown in FIG. 2a, flexion is when the angle θ is positive or the knee is "bent." FIG. 2b, illustrates the knee in hyperextension i.e, when the angle θ defined by the femur and the tibia goes beyond zero and into the negative range. Typically when an average person stands and "locks" out his knees, his knees are in hyperextension. Advantages of an equiangular distal and posterior bone interface as defined above includes a more bone conserving implant geometry and control of implant thickness across the major regions of the implant, i.e., flexion, mid-flexion, and extension regions.

Having a unicondylar femoral knee component 100 with a single sagittal radius of curvature allows for better adaptation of femoral/tibial articulation to meet the load and performance requirements of regional patients, i.e., patients from various regions such as Europe, USA, Asia, Latin America, etc. A single sagittal radius of curvature allow for easier adaptation of femoral/tibial articulation by varying the medial/lateral radius of the femoral knee component or by varying the medial/lateral radius of the corresponding tibial bearing component or by some combination of both.

Figure 3:
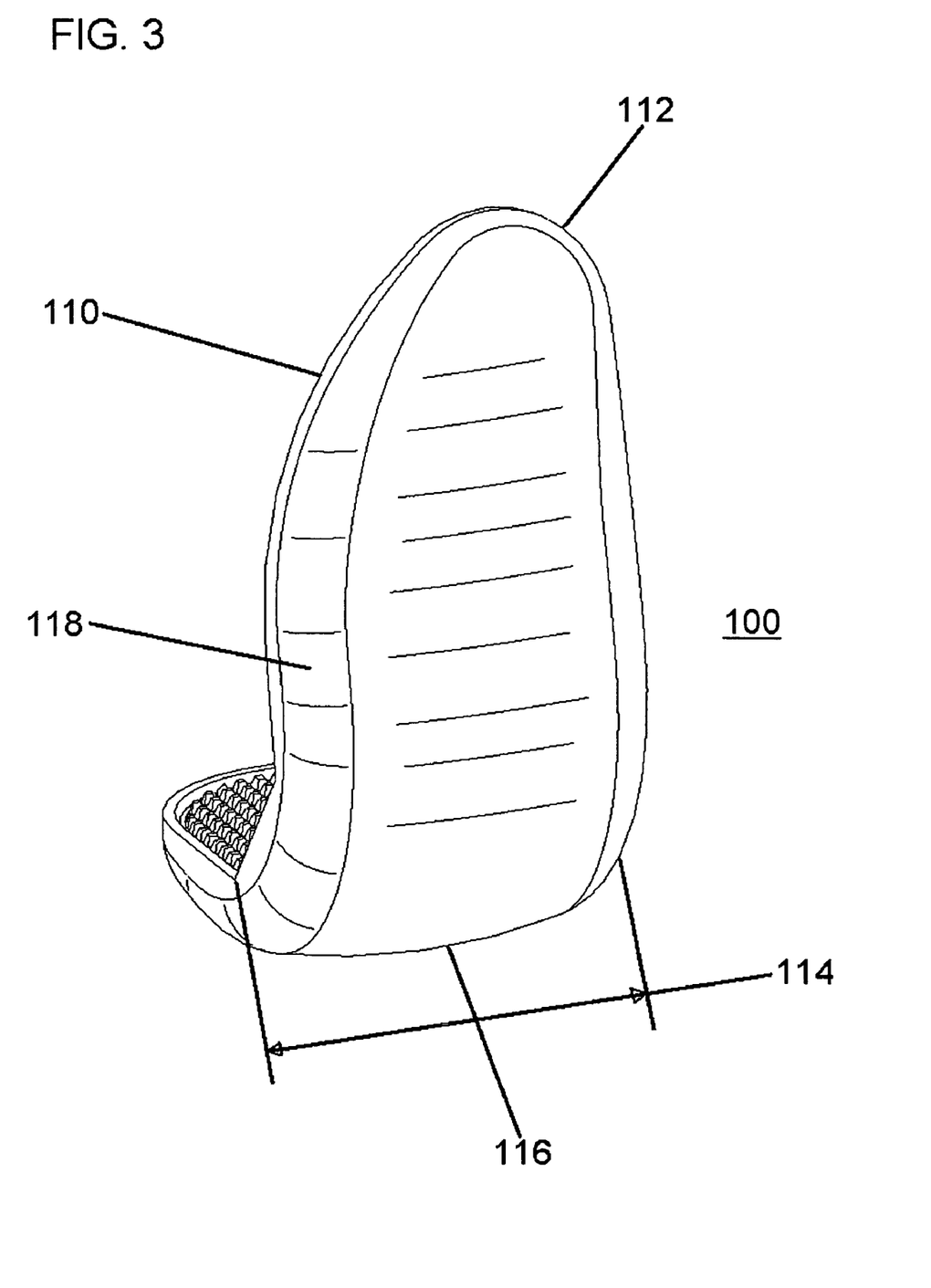
FIG. 3 is a perspective anterior/medial view of the embodiment of the unicondylar femoral knee implant of FIG. 1.

The unicondylar femoral knee component 100 of the present embodiment, as shown in FIG. 3 in a perspective anterior/medial view, has a single medial/lateral ("M/L") radius 116 of about 38 mm that sweeps through the entire single sagittal radius to define the articulating surface. The femoral knee component 100 also has relatively large transitional radii 118 at the edges. The anterior/medial curvature 110 of the femoral component can have an anteriorly tapered curvature to allow good coverage of the bone without anterior overhang. The anterior/lateral curvature 112 has a non-tapered configuration to provide good coverage of the bone without anterior overhang or patellar interference. The medial/lateral width 114 is designed to provide good bone coverage without patella interference. The resulting configuration results in a distal geometry that better matches the anatomy of patients from various regions. Patients from various regions are known to have variations in knee anatomy, more specifically patients from various regions have different anterior to posterior:medial to lateral (A/P:M/L) ratios of length. The present inventive system is designed to provide bone coverage taking into account these variations in A/P:M/L ratios.

Figure 4:
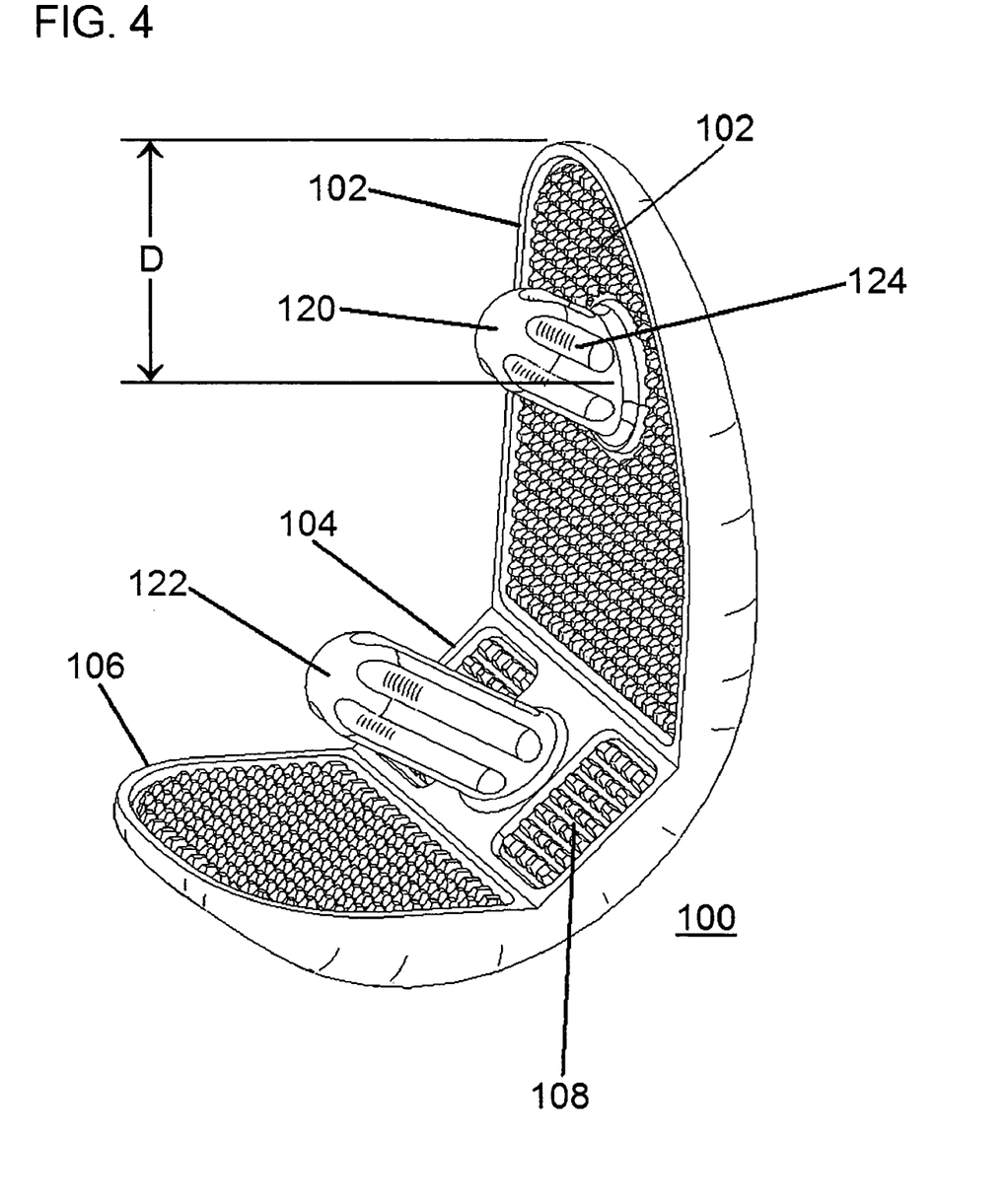
FIG. 4 is perspective view of another embodiment of a unicondylar femoral knee implant of the present invention.

The unicompartmental femoral knee component 100 can also include fixation members. The fixation members can be of any shape such as a cylindrical peg. FIG. 4 shows another embodiment that includes first and second fixation pegs 120, 122, respectively. The first fixation peg 120 protrudes from the distal bone interface surface 102 and the second fixation peg 122 protrudes from the distal-to-posterior chamfer bone interface surface 104. The axes of the fixation pegs 120, 122 are parallel and coplanar to a plane normal to all three bone interface surfaces 102, 104, 106. The axes of the fixation pegs 120, 122 are angled at about 25 degrees with respect to the posterior bone interface surface 106. The angle of the fixation pegs can range from about 20 degrees to about 30 degrees.

Each fixation peg can also contain a plurality of axial "flutes" 124 to further increase the surface area e.g., for either cemented or press-fit applications. The femoral knee component can also be configured to include only one fixation member extending from any region of the bone interface surface. In the present embodiment the bone interface surfaces 102, 104, 106 are optionally shown to include a waffle pattern 108 to enhance the surface area of the interface surface. However, other types of surfacing are equally possible as described below.

The about 25 degree angle of the fixation pegs 120, 122 of the present embodiment advantageously allows the femoral component to be implanted using an anterior approach. Moreover, the about 25 degree angle is especially advantageous when implanting the femoral component using a minimally invasive surgical approach where the incision is small and consequently exposure of the knee joint is small.

Another aspect of the present invention includes positioning the fixation member (e.g., peg 120) at a fixed position relative to the anterior aspect of the unicondylar femoral knee implant 100 for all femoral implant sizes. Referring back to FIG. 4, the first fixation peg 120 is at a fixed position at a predetermined constant distance D from the anterior aspect of the unicondylar femoral knee implant 100. Maintaining the fixation member 120 at a fixed or constant position relative to the anterior aspect of the unicondylar femoral knee implant 100 for all femoral implant sizes allows for an easier transition when changing sizes. Typically, knee implants are good in extension and tight in flexion when assessing a knee during trialing or the trial phase. Accordingly, a larger or smaller size implant may be required, thus necessitating the need for additional bone cuts. However, with the present inventive unicondylar femoral knee implant 100, the need for additional distal resections is substantially eliminated for a knee tight in flexion, resulting in a simplification of the overall technique required to intraoperatively change implant sizes.

A unicondylar femoral knee implant component made in accordance with the present invention can be made from any suitable biocompatible material, such as titanium, commercially pure titanium or titanium alloy, cobalt chromium alloy, nickel-cobalt, ceramics, or stainless steel. The unicondylar femoral knee component 100 can also be configured to have a bone engaging surface texture such as prismatic pattern, waffle pattern, porous structures, insets, recesses, or the like to increase the surface area for either cemented or press-fit applications. The present inventive femoral components can also be coated with biologic substances such as osteoinductive (e.g., Osteogenic Protein-1 (OP1)) and/or osteoconductive materials (e.g., hyrdoxyapatite) that facilitates fixation of the implant to bone. However, any surface texture that allows on-growth or in-growth of the bone may also be used.

Figure 5:
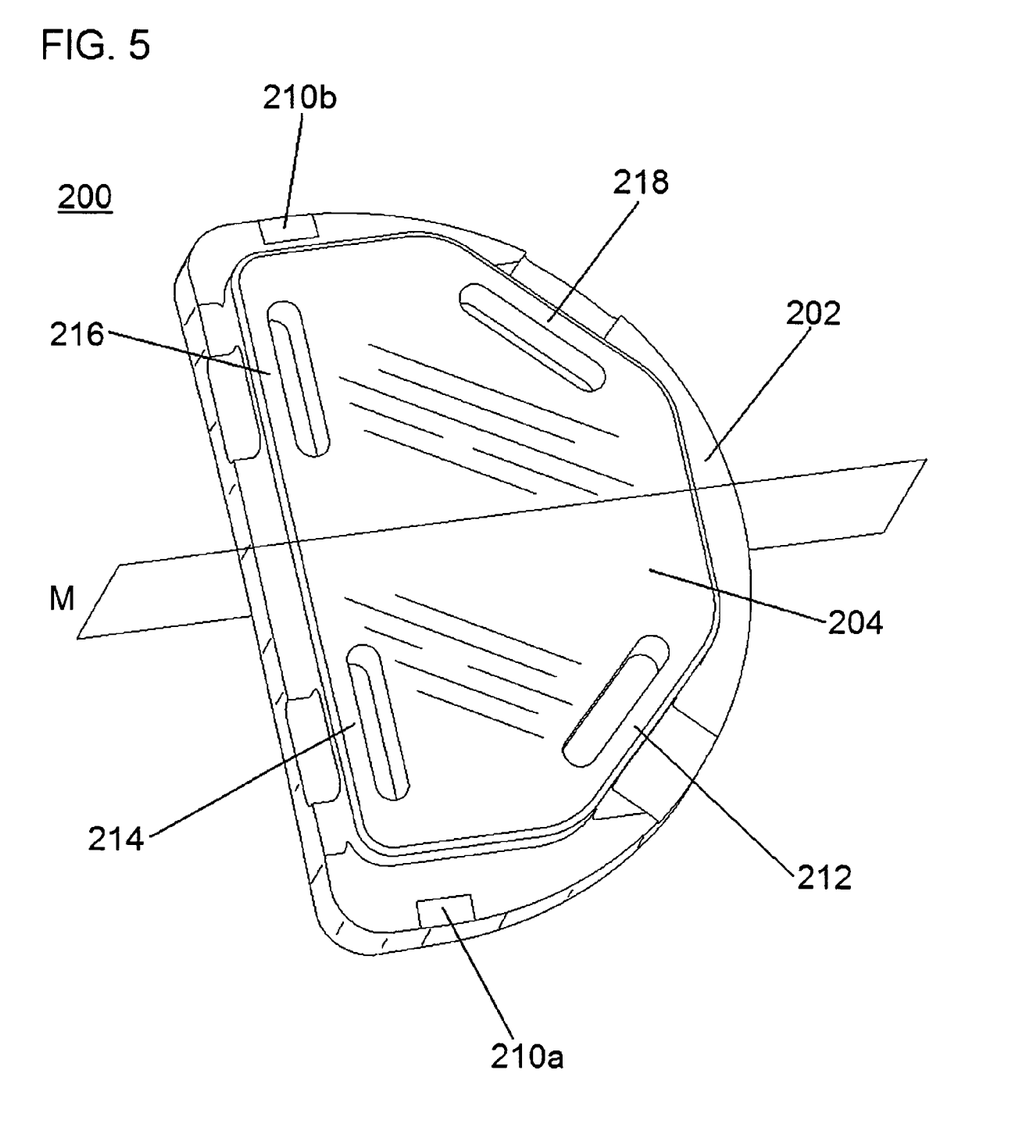
FIG. 5 is a perspective inferior view of an embodiment of a tibial bearing implant of the present invention.
Figure 6:
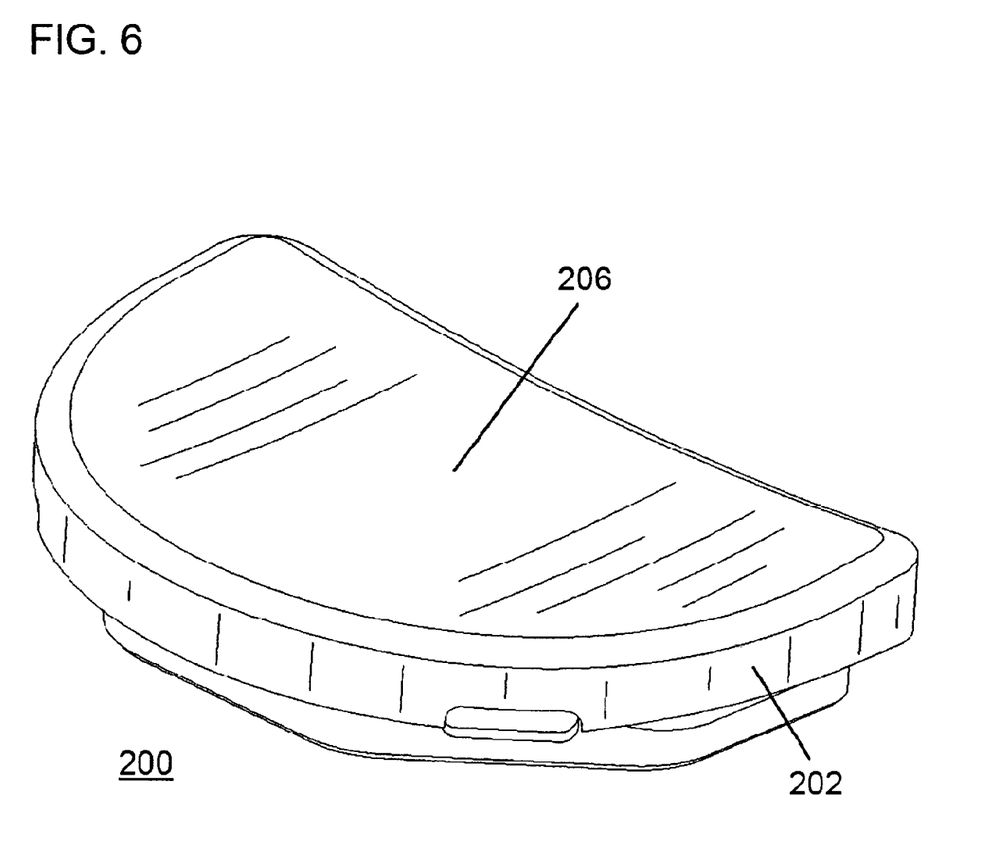
FIG. 6 is a perspective superior view of the embodiment of the tibial bearing implant of FIG. 5.
Figure 7:
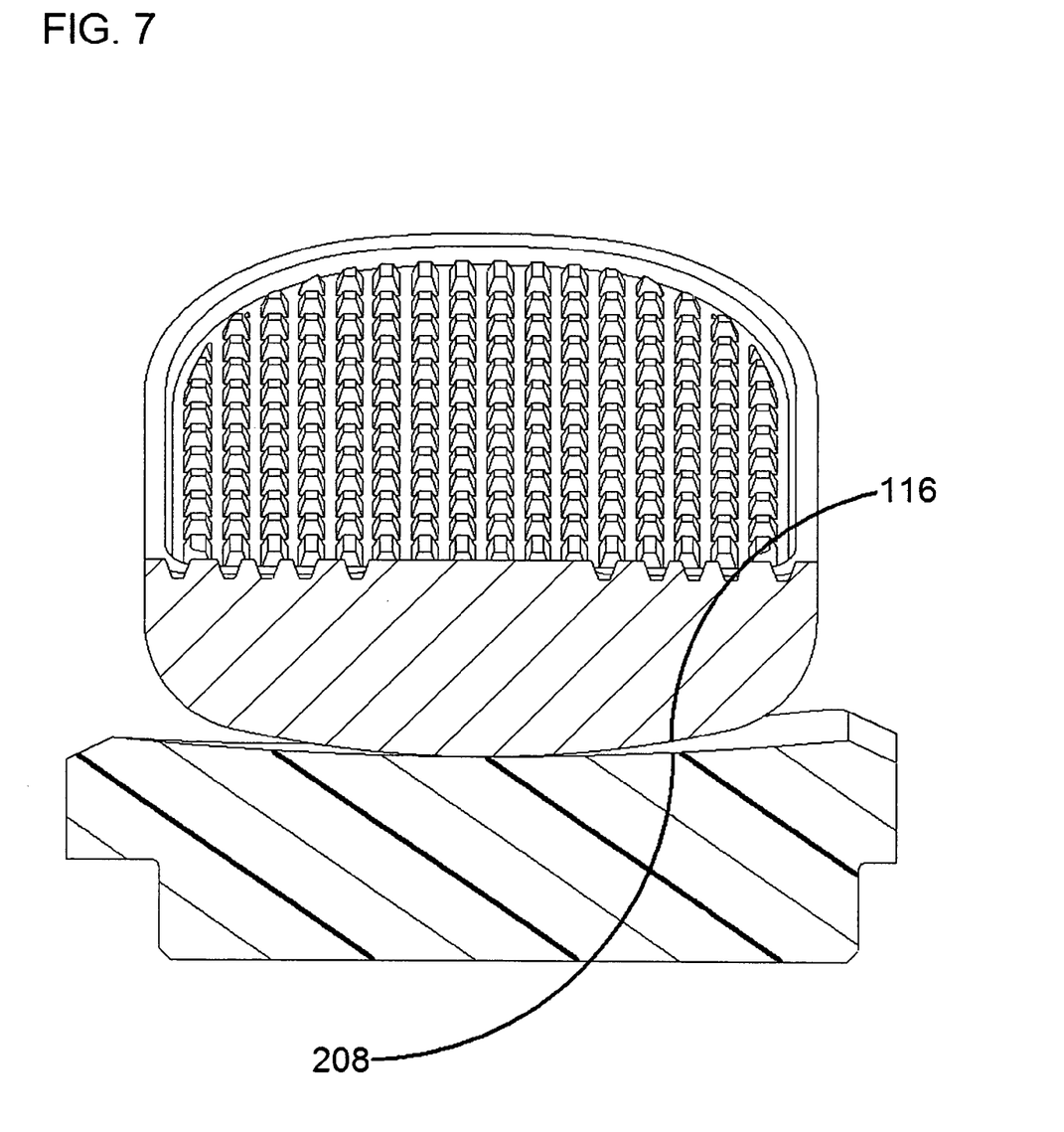
FIG. 7 is a posterior view of the unicondylar femoral knee implant of FIG. 1 assembled to the tibial bearing implant of FIG. 5 at full extension.
Figure 9A:
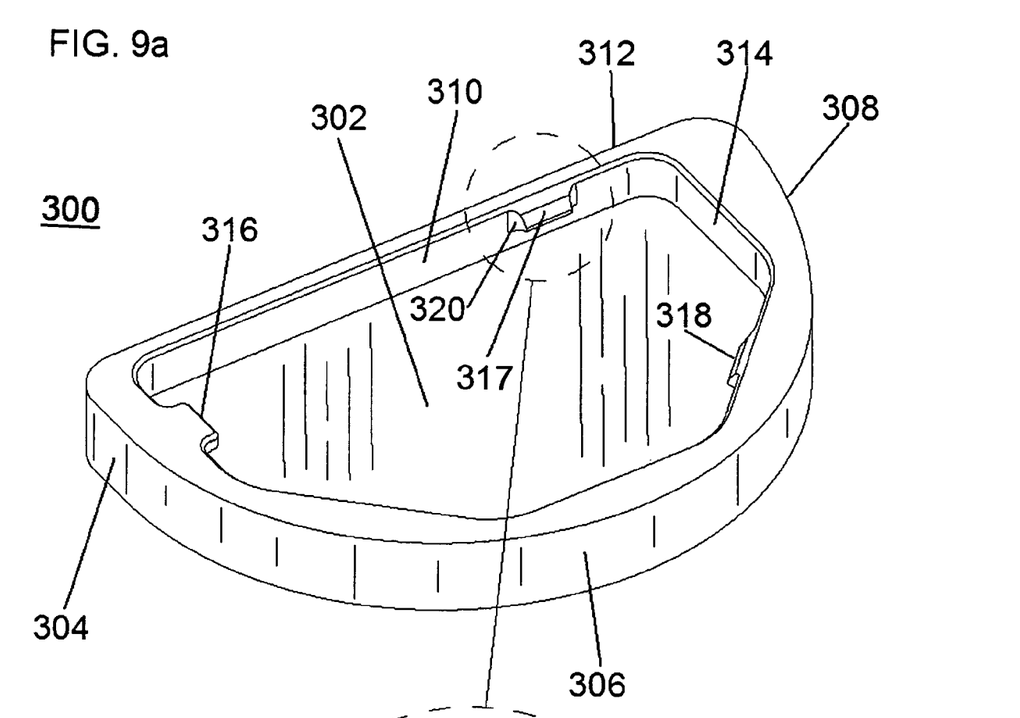
FIG. 9a is perspective superior view of an embodiment of a tibial tray implant of the present invention.

FIGS. 5 and 6 illustrate an embodiment of a tibial bearing component 200 according to the present invention. FIG. 5 illustrates a perspective inferior view of the tibial bearing component. The tibial bearing component 200 has a top portion 202 and a bottom portion 204. The tibial bearing component 200 is symmetric about a midline plane M and can be used for either a right or left knee. The top portion 202 has a superior articulating surface 206 that articulates with a corresponding unicondylar femoral knee component 100, as shown in a perspective superior view in FIG. 6. The top portion 202 is anatomic in shape and approximately matches the outside shape of a corresponding tibial tray component 300 (FIG. 9a). The tibia bearing articulating surface 206 has a single medial/lateral radius 208 as shown in FIG. 7 and an elliptical anterior/posterior radius i.e., the single sagittal radius (not shown). In an embodiment, the medial/lateral radius of the tibial bearing articulating surface 208 is about 127 mm. When the tibial bearing component is mated with a corresponding unicondylar femoral knee component 100 having a single medial/lateral radius 116 of about 38 mm, the resulting system advantageously allows for plus or minus about 10 degrees of varus/valgus misalignment and a decreasing amount of constraint at higher degrees of flexion.

Referring again to FIG. 5, the bottom portion 204 of the tibial bearing component 200 is geometric and matches the inside shape of the mating tibial tray component 300 (FIG. 9a). The bottom portion 204 has an undercut 210a, 210b on the posterior and anterior aspects. During engagement with the tibial tray component 300, the undercut 210a or 210b will engage a corresponding posterior lip 316 (FIG. 9a), on the posterior aspect of the peripheral vertical rim 310 of the tibial tray component 300, depending upon whether the implant is implanted into the left or right knee. The bottom portion 204 also has four flexible catches 212, 214, 216, 218 to receive corresponding latches 317, 318 on the tibial tray component 300 (FIG. 9a). The catches 212, 214, 216, 218 are used to secure the tibial bearing component 200 onto the tibial tray component 300. In the present embodiment the catches 212, 214, 216, 218 are positioned as shown in FIG. 5 and only engage two latches 317, 318 on the tibial tray component 300 (FIG. 9a). The additional two catches are available to allow the implant to be used in either a right or left configuration.

Figure 8:
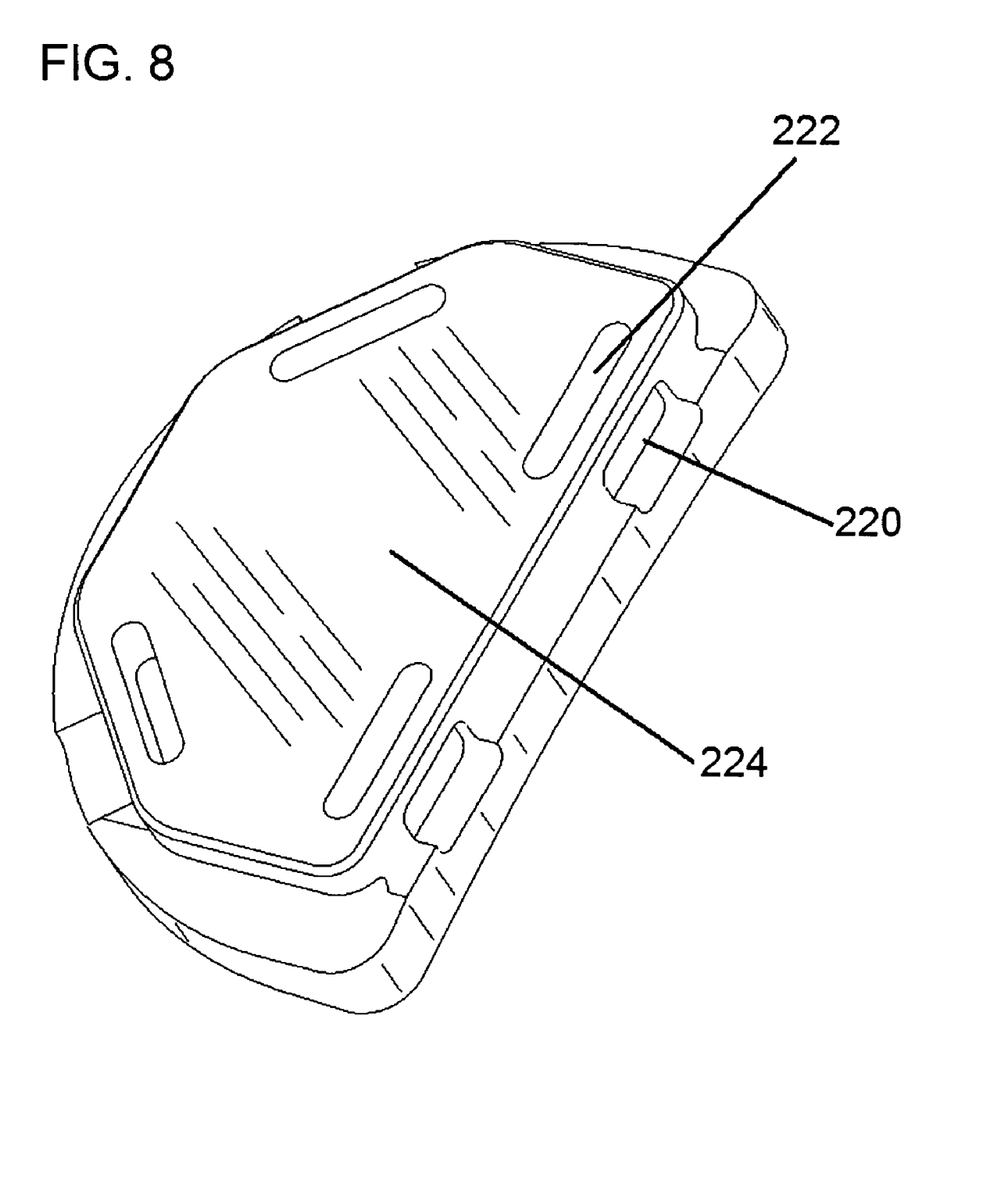
FIG. 8 is a perspective inferior view of the embodiment of the tibial bearing implant of FIG. 5.

The catches 212, 214, 216, 218 are formed within the bottom portion of the tibial bearing implant component. As shown in FIG. 8, each catch has an opening 220 in the bottom portion of the tibial bearing component 300 such that the opening 220 faces the peripheral vertical rim 310 of the tibial tray component 300 when seated. The opening 220 is in fluid communication with a second opening 222 on the distal surface 224 of the tibial bearing component 300. The resulting configuration of the two openings 220, 222 results in a flexible catch.

The flexible catches 212, 214, 216, 218 are positioned to catch or latch onto corresponding protrusions or latches 316, 318, on the tibial tray component 300. The flexible catches 212, 214, 216, 218 allows for the tibial bearing to be press-fitted onto the tibial tray component 300 for secure fixation of the tibial bearing to the tibial tray component. The tibial bearing component 200 allows for insertion onto the tibial tray component 300 by applying a predominately posteriorly directed force, thus enabling the assembly of the tibial bearing 200 and the tibial tray 300 to be more compatible with a MIS surgical approach.

The tibial bearing component 200 can be made from any suitable material, such as ultra-high molecular weight polyethylene ("UHMWPE"), ceramics, or other suitable polymers.

The tibial bearing 200 is assembled or attached onto the tibial tray 300 to form a tibial knee prosthesis. The assembly can take place either before or after implantation of the tibial tray 300 into the prepared tibia. A preferred technique for fixing or seating the tibial bearing 200 onto the tibial tray 300 is to slide the tibial bearing 200 onto the tibial tray 300 from the anterior direction so as to engage the tibial tray's posterior lip 316. After engagement of the posterior lip 316, a slight anterior-downward force is applied to the anterior portion of the tibial bearing 200 to snap the tibial bearing 200 onto the tibial tray 300. The flexible catches and undercuts of the tibial bearing 200 forms part of the tibial prosthesis's locking mechanism.

An advantage of the present invention is that the mutually engaging bearing surfaces of the femoral component 100 and the tibial bearing component 200 provides better contact stress where the loads are greater and less constraint where more motion is necessary. Another advantage is that the articulation between the femur and tibia allows for a high degree of anterior clearance during flexion and good femoral-tibial contact throughout the entire range of motion. An advantage of the tibial bearing 200 is that the flexible catches allows for a tight assembly onto the tibial tray by allowing the flexible catches to deflect during insertion and take up laxity after catching the latches. Yet another advantage is that the tibial bearings are symmetric, thus reducing the amount of inventory required for a unicondylar implant system. An advantage of the tibial prosthesis's locking mechanism is that the design eliminates the need for any third body locking feature, such as a metal wire or ring, which makes the tibial prosthesis more compatible with gas sterilization techniques and reduces micromotion as a result of third-body wear.

FIG. 9a illustrates a tibial tray component 300 according to one embodiment of the present invention. FIG. 9a is a perspective superior view of the tibial tray component 300. The tibial tray 300 includes a tray member 302 and a keel 322 (shown in FIG. 10). The tray member 302 has a peripheral vertical rim 310 with an exterior profile defined by a posterior curvature 304, medial curvature 306, an anterior curvature 308, and a medial section 312. This overall profile provides good cortical bone coverage without overhang in the posterior, medial, or anterior aspects. The tibial tray geometry 300 is designed to match regional anatomy (e.g., patients from Europe, USA, Asia, Latin America, etc.) and can be adapted region-by-region.

Figure 9B:
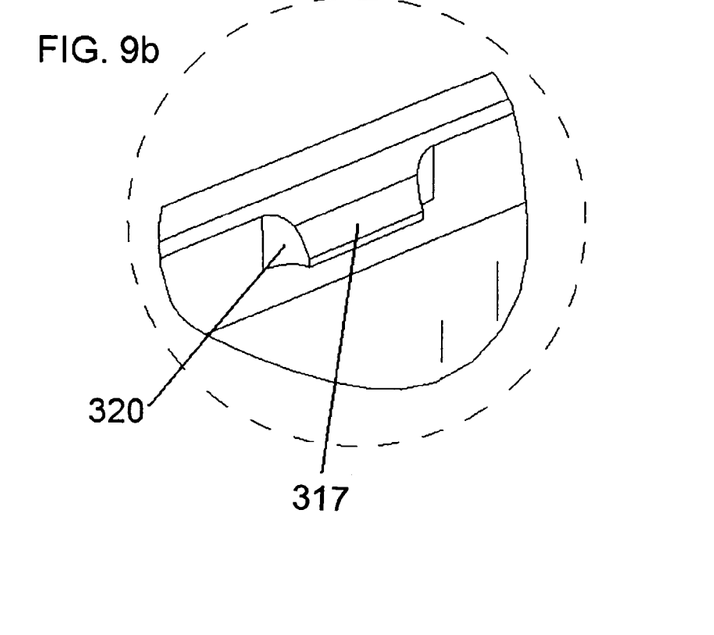

The interior profile 314 of the peripheral vertical rim 310 is configured as shown in FIG. 9a and matches the bottom portion 204 geometry of the tibial bearing component 200. A protrusion or lip 316 is positioned on the posterior aspect of the tibial tray 300 that extends inwards from the upper most portion of the peripheral vertical rim 310. The tray member 302 also has two latches 317, 318, that protrude inward from the peripheral vertical rim 310. The latches 317, 318, are positioned to correspond in position with the catches 212, 214, or 216, 218 on the tibial bearing component 200 depending on whether a right or left knee is being operated on. The latches may also be chamfered 320, for example at about 30 degrees, to allow for easier insertion of the tibial bearing component, as shown in FIG. 9b.

Figure 10:
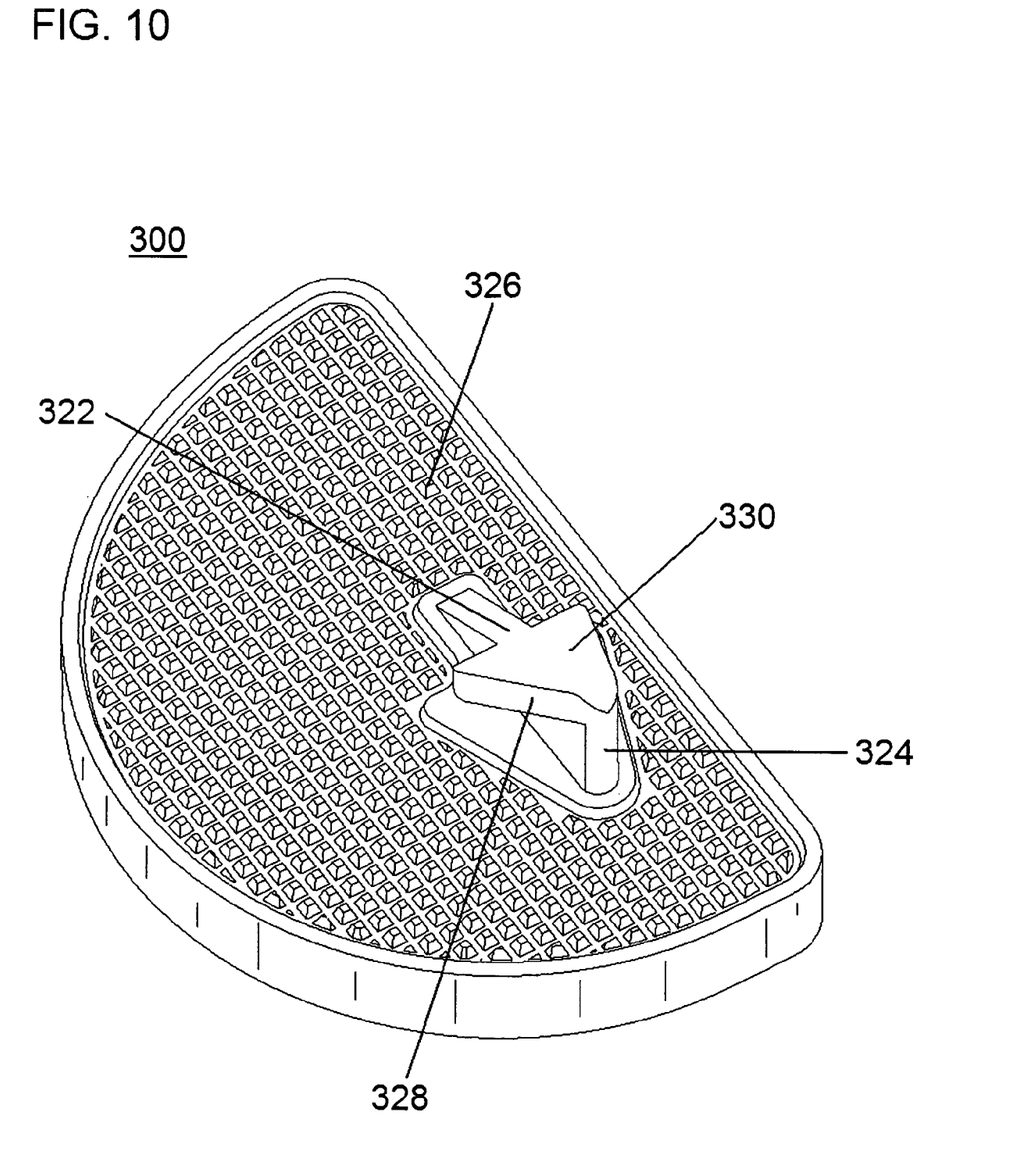

FIG. 10 is a perspective view of the inferior side or underside of the tibial tray component 300. Orientation references such, as medial or lateral, are given assuming the device is implanted in the medial femoral compartment of the left knee. The same tibial tray 300 can be implanted in the lateral compartment of the opposite knee.

According to one embodiment, the tibial tray component 300 has a tibial keel 322. The tibial keel 322 has a vertical keel section 324 extending from the inferior surface 326 of the tibial tray 300 to a keel foot region 328. The keel foot region 328 has a bottom planar surface 330 angled at about 30 degrees relative to the inferior surface 326 of the tibial tray 300 so as to form a down-plane or posterior slope. The term down-plane is used herein to describe the keel foot region being at an angle relative to the inferior surface of the tibial tray. The keel foot 328 is shaped to have a posterior taper, so as to have a tapered angle leading from the anterior aspect to the posterior aspect of the keel foot 328, i.e., the anterior aspect being wider than the posterior aspect. The angle of the keel foot 328 can be any angle less than 90 degrees relative to the inferior surface of the tibial bearing tray 326 so as to maintain a horizontal aspect of the keel foot region 328. A horizontal aspect is maintained so long as when describing the angle of the foot region relative to the inferior surface 326 of the tibial tray 300 in X-Y coordinates, the X coordinate value is greater than zero. In one embodiment, the keel foot region 328 can be in the shape of a planar isosceles triangle. The shape of the keel foot region 328 is described for illustrative purposes and not for purposes of limitation. The shape of the keel foot region 328 can be of any configuration that results in a narrowing of the posterior aspect of the foot region, such as that of a "Danforth®" style boat anchor.

The tibial keel 322 can be used with any device, such as a tibial prosthesis for a total knee implant; its use is not limited to unicondylar knee implant systems.

The tibial keel 322 is a self-locking keel that provides resistance to anterior and posterior translation, liftoff, and subsidence as a result of its keel foot design. The horizontal aspect of the keel foot 328 resists liftoff and subsidence. The vertical aspect of the keel foot 328 resists anterior and posterior motion.

The downward angled keel foot 328 allows the tibial tray component 300 to be implanted from the anterior aspect of the knee joint so as to be compatible with a MIS surgical approach. The downward angled keel foot 328 also provides a securing or clamping force to further secure the tibial tray component 300 to the prepared proximal tibia bone. The tibial tray component 300 also allows for implantation of the tibial tray component 300 onto the prepared tibia by applying a force predominantly in the posterior direction. Thus, the tibial tray 300 advantageously eliminates or minimizing the need for a force normal to the prepared tibia to implant a tibial bearing component. Consequently, the amount of expose required for a unicompartmental knee implant surgery is further minimized.

Figure 11:
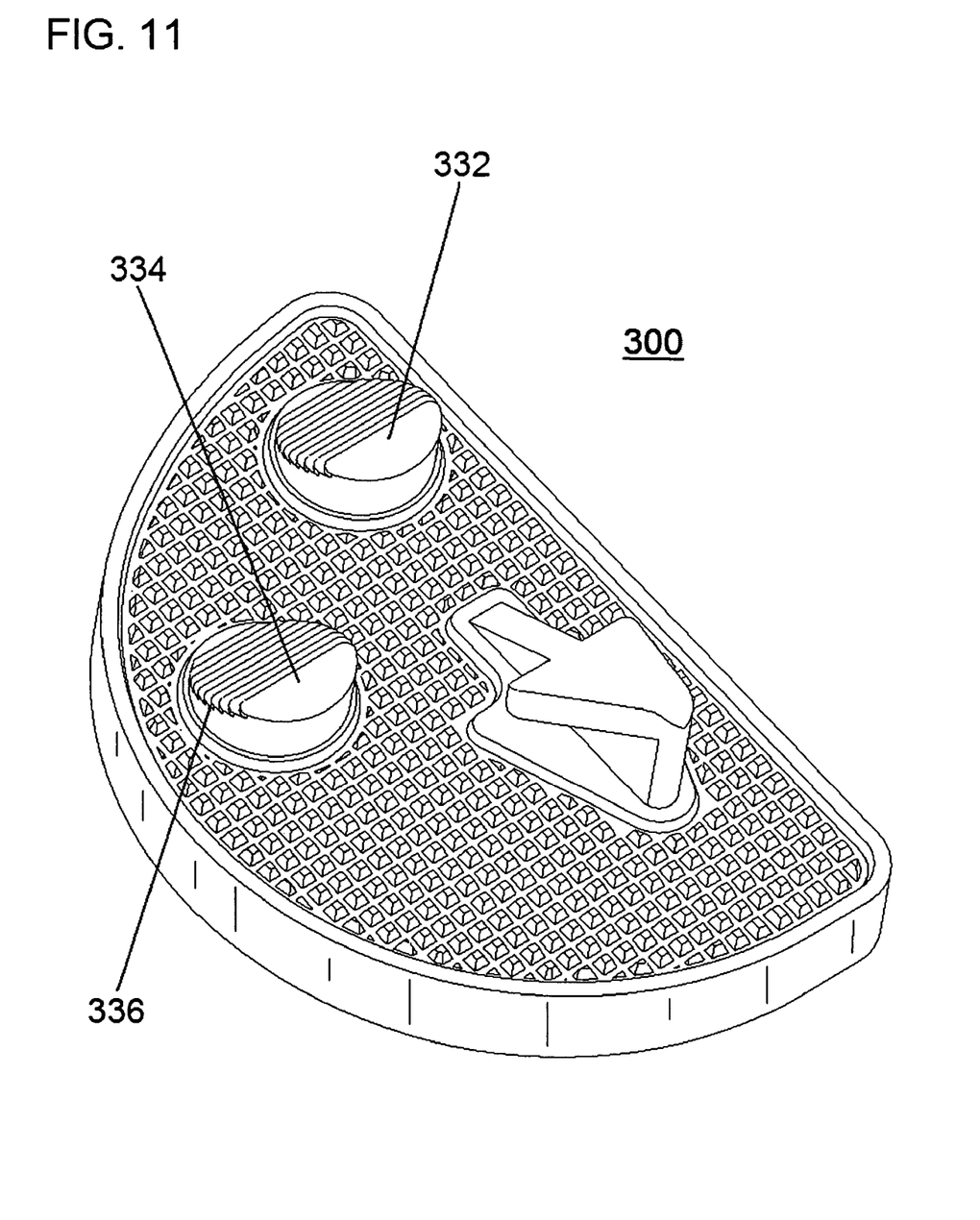
FIG. 11 is a perspective inferior view of another embodiment of a tibial tray implant of the present invention.

The illustrated and described tibial tray can also include keel pegs 332, 334 as shown in another embodiment in FIG. 11. The pegs 332, 334 can further include normalizations 336 for additional fixation when implanted. Normalizations 336 are step-like contours along the surface of the pegs.

A tibia tray component made in accordance with one of the present embodiments can be made from any suitable biocompatible material such as titanium, titanium alloy, commercially pure titanium, cobalt chromium alloy, nickel-cobalt, ceramics, or stainless steel. The tibial tray component can also be configured to have a bone engaging surface texture, such as a prismatic pattern, waffle pattern, porous structures, insets, recesses, or the like to increase the surface area for either cemented or press-fit fixation. Biologics, such as osteoinductive (e.g., OP1) and/or osteoconductive materials (e.g., hyrdoxyapatite) that facilitates fixation of the implant to bone, can also be added to the bone engaging surfaces of the tibial tray component. However, any surface texture that allows on-growth or in-growth of the bone may also be used.

The tibial implant prosthesis can also be made as an all-poly one piece construction. That is the tibial bearing component and the tibial bearing component is unitized and fully constructed from a polymeric material.

The embodiments of the present invention are shown and described for purposes of illustration only and not for purposes of limitation. While there have been shown, described, and pointed out fundamental novel features of the invention as applied to several embodiments, it will be understood that various omissions, substitutions, and changes in the form and details of the devices illustrated, and in their operation, may be made by those skilled in the art without departing from the spirit and scope of the invention. Substitutions of elements from one embodiment to another are also fully intended and contemplated. It is also to be understood that the drawings are not necessarily drawn to scale, but that they are merely conceptual in nature. The invention is defined solely with regard to the claims appended hereto, and equivalents of the recitations therein.

The above mentioned patents, applications, test methods, and publications are hereby incorporated by reference in their entirety.

What is claimed is:

1. A unicondylar knee prosthesis comprising:
   a tibial bearing component including:
      a top portion having an articulating surface; and
      a bottom portion connected to the top portion; and
   a tibial tray component including:
      a tray member; and
      a keel connected to a distal surface of the tray member wherein the keel includes:
         a vertical keel section extending from the distal surface of the tray member, wherein the vertical keel section has a horizontal dimension; and
         a posterior sloped and posterior tapered keel foot having a tapered angle leading from an anterior aspect to a posterior aspect of the keel foot, such that the anterior aspect is closer to a front of the knee prosthesis than, and wider than, the posterior aspect, extending horizontally away from the vertical keel section, and spaced away from the distal surface of the tray member, thereby the keel foot defining a horizontal dimension, wherein said horizontal dimension of said keel foot is larger than said horizontal dimension of said vertical keel section; and wherein the tibial tray component is to be implanted into a prepared tibia and the tibial bearing component is to be attached to the tibial tray component.

2. The unicondylar knee prosthesis of claim 1, further comprising a locking mechanism attaching the tibial bearing component and the tibial tray component.

3. The unicondylar knee prosthesis of claim 2, wherein the locking mechanism comprises:
a peripheral vertical rim on the tibial tray component; at least one latch extending from the peripheral vertical rim; and at least one flexible catch on the bottom portion of the tibial bearing component engaging the at least one latch so as to attach the tibial bearing component to the tibial tray component.

4. The unicondylar knee prosthesis of claim 3, wherein the flexible catch comprises an opening on the bottom portion of the tibial bearing component facing the peripheral vertical rim of the tibial tray component and the opening is in fluid communication with a second opening on a distal surface of the bottom portion.

5. The unicondylar knee prosthesis of claim 3, wherein the locking mechanism comprises two latches engaging two flexible catches.

6. The unicondylar knee prosthesis of claim 1, further comprising a femoral component operatively associated with the tibial bearing component.

7. The unicondylar knee prosthesis of claim 6, wherein the femoral component further comprises: a posterior flange; and at least one peg engaging a distal femur, wherein the peg is angled relative to the posterior flange.

8. The unicondylar knee prosthesis of claim 7, wherein the peg is angled at about 25 degrees relative to the posterior flange.

9. The unicondylar knee prosthesis of claim 7, including two substantially parallel pegs angled about 25 degrees from the posterior flange.

10. The unicondylar knee prosthesis of claim 6, wherein the articulating surface further comprises a single medial-lateral radius.

11. The unicondylar knee prosthesis of claim 10, wherein the single medial-lateral radius is about 38 mm.

12. The unicondylar knee prosthesis of claim 6, wherein the femoral component further comprises a biological coating.

13. The unicondylar knee prosthesis of claim 12, wherein the biological coating is at least one of hydroxyapatite and Osteogenic Protein-1 (OP1).

14. The unicondylar knee prosthesis of claim 6, wherein the femoral component further comprises: a bone engaging surface including:
a distal surface; a posterior surface; a distal-to-posterior chamfer surface disposed between the distal surface and the posterior surface; and wherein the distal surface and the posterior surface are equiangular to the distal-to-posterior chamfer surface; and an articulating surface comprising a single sagittal radius of curvature from about 10 degrees of hyperextension to about 140 degrees of flexion.

15. The unicondylar knee prosthesis of claim 14, wherein the femoral component further comprises:
a posterior flange; and
at least one peg engaging a distal femur, wherein the peg is angled relative to the posterior flange.

16. The unicondylar knee prosthesis of claim 15, wherein the at least one peg is angled at about 25 degrees relative to the posterior flange.

17. The unicondylar knee prosthesis of claim 15, further comprising two substantially parallel pegs angled about 25 degrees from the posterior flange.

18. The unicondylar knee prosthesis of claim 14, wherein the articulating surface further comprises a single medial-lateral radius.

19. The unicondylar knee prosthesis of claim 18, wherein the single medial-lateral radius is about 38 mm.

20. The unicondylar knee prosthesis of claim 14, further comprising a biologic coating.

21. The unicondylar knee prosthesis of claim 20, wherein the biological coating is at least one of hydroxyapatite and Osteogenic Protein-1 (OP1).

22. The unicondylar knee prosthesis of claim 6, wherein the femoral component comprises:
a bone engaging surface; and
an articulating surface comprising a single sagittal radius of curvature from about 10 degrees of hyperextension to about 140 degrees of flexion.

23. The unicondylar knee prosthesis of claim 22, wherein the bone engaging surface comprises: a distal surface; a posterior surface; a distal-to-posterior chamfer surface disposed between the distal surface and the posterior surface; and wherein the distal surface and the posterior surface are equiangular to the distal-to-posterior chamfer surface.

24. The unicondylar knee prosthesis of claim 1, wherein the tibial tray component further comprises a biological coating.

25. The unicondylar knee prosthesis of claim 24, wherein the biological coating is at least one of hydroxyapatite and Osteogenic Protein-1 (OP1).

26. The unicondylar knee prosthesis of claim 1, further comprising:
at least two unicondylar femoral knee implants each including:
a distal bone engaging surface having an anterior end;
a posterior bone engaging surface;
a distal-to-posterior chamfer bone engaging surface disposed between the distal and the posterior bone engaging surface, wherein the distal surface and the posterior bone engaging surface are equiangular to the distal-to-posterior chamfer bone engaging surface.

27. The unicondylar knee prosthesis of claim 26, wherein the at least two unicondylar femoral knee implants further includes an articulating surface comprising a single sagittal radius of curvature from about 10 degrees of hyperextension to about 140 degrees of flexion.

28. The unicondylar knee prosthesis of claim 26, wherein the at least two unicondylar femoral knee implants further includes at least one peg extending from the distal bone engaging surface at a constant distance from the anterior end for the at least two unicondylar femoral knee implants.

29. The unicondylar knee prosthesis of claim 27, wherein the at least two unicondylar femoral knee implants further includes at least one peg extending from the distal bone engaging surface at a constant distance from the anterior end for the at least two unicondylar femoral knee implants.

30. The unicondylar knee prosthesis of claim 1, wherein the keel foot secures the tibial tray component to the prepared tibia.

31. A keel for a medical device for implantation in a knee comprising:
a vertical keel section for extension from a surface of the device, wherein the vertical keel section has a horizontal dimension and the keel is to be implanted into a prepared tibia and a posterior sloped and posterior tapered keel foot having a tapered angle leading from an anterior aspect to a posterior aspect of the keel foot, such that the anterior aspect is closer to a front of the keel than, and wider than, the posterior aspect, extending horizontally away from the vertical keel section, and spaced away from the distal surface of the tray member, wherein said keel foot has a horizontal dimension and wherein said horizontal dimension of said keel foot is larger than said horizontal dimension of said vertical keel section.

32. The keel of claim 31, wherein the device is an orthopedic tibial prosthesis for a unicondylar knee implant.

33. The keel of claim 32, wherein the tibial prosthesis is implanted from an anterior approach.

34. The keel of claim 31, wherein the device is an orthopedic tibial prosthesis for a total knee implant.

35. The keel of claim 31, further comprising a biological coating.

36. The keel of claim 35, wherein the biological coating is at least one of hydroxyapatite and Osteogenic Protein-1 (OP1).

37. The keel of claim 31, wherein the device is a tibial knee prosthesis comprising: a tibial tray component including: a tray member including: a peripheral vertical rim on the tray member; a posterior lip extending from a posterior aspect of the peripheral vertical rim; and at least one latch extending from the peripheral vertical rim proximally substantially towards a center of the tray member and away from the peripheral vertical rim; and a tibial bearing component including: a top portion having an articulating surface; and a bottom portion connected to the top portion shaped to fit securely within the peripheral vertical rim of the tray member, including: a posterior wedge engaging the posterior lip; and at least one flexible catch engaging the at least one latch, wherein the flexible catch comprises an opening on the bottom portion of the bearing component facing the peripheral vertical rim of the tibial tray component and the opening is in fluid communication with a second opening on a distal surface of the bottom portion.

38. The keel of claim 37, wherein the tibial tray component includes four latches engaging four flexible catches on the tibial bearing component.

39. The keel of claim 37, further comprising a biologic coating.

40. The keel of claim 39, wherein the biological coating is at least one of hydroxyapatite and Osteogenic Protein-1 (OP1).

41. The keel of claim 31, wherein the keel foot has a planar surface.

42. The keel of claim 41, wherein the vertical keel extends lengthwise in an anterior to posterior direction.

43. The keel of claim 31, wherein the keel foot is wider than the width of the vertical keel section.

44. The keel of claim 31, wherein the keel has a cross-section about a coronal plane in the shape of a cross.

45. The keel of claim 31, wherein the vertical keel section is a planar section.

46. A unicondylar knee implant system comprising:
at least two unicondylar femoral knee implants each including:
a distal bone engaging surface having an anterior end;
a posterior bone engaging surface;
a distal-to-posterior chamfer bone engaging surface disposed between the distal and the posterior bone engaging surface; and
at least one peg extending from the distal bone engaging surface at a constant distance from the anterior end for the at least two unicondylar femoral knee implants; and
at least two unicondylar tibial tray implants each including:
a tray member; and
a keel connected to a distal surface of the tray member, that includes:
a vertical keel section extending from the distal surface of the tray member, wherein the vertical keel section has a horizontal dimension; and
a posterior sloped and posterior tapered keel foot having a tapered angle leading from an anterior aspect to a posterior aspect of the keel foot, such that the anterior aspect is closer to a front of the system than, and wider than, the posterior aspect, extending horizontally away from the vertical keel section, and spaced away from the distal surface of the tray member, wherein said keel foot has a horizontal dimension and wherein said horizontal dimension of said keel foot is larger than said horizontal dimension of said vertical keel section.

\* \* \* \* \*